United States Patent
Cheng (10) Patent No.: US 11,452,917 B2
(45) Date of Patent: Sep. 27, 2022

(54) RUNNING PARAMETERS DETECTION SYSTEM FOR TREADMILLS AND DETECTION METHOD THEREOF

(71) Applicant: WECATCHUP INC., Tainan (TW)

(72) Inventor: Chiao-Ling Cheng, Tainan (TW)

(73) Assignee: WECATCHUP INC., Tainan (TW)

( * ) Notice: Subject to any disclaimer, the term of this patent is extended or adjusted under 35 U.S.C. 154(b) by 162 days.

(21) Appl. No.: 16/879,964

(22) Filed: May 21, 2020

(65) Prior Publication Data

US 2020/0376341 A1 Dec. 3, 2020

(30) Foreign Application Priority Data

May 30, 2019 (TW) ................................ 10811879.0

(51) Int. Cl.
*A63B 24/00* (2006.01)
*A63B 22/02* (2006.01)
*A63B 69/00* (2006.01)

(52) U.S. Cl.
CPC ........ *A63B 24/0087* (2013.01); *A63B 22/025* (2015.10); *A63B 69/0028* (2013.01); *A63B 2024/0093* (2013.01); *A63B 2220/22* (2013.01); *A63B 2220/40* (2013.01)

(58) Field of Classification Search
USPC .......................................................... 482/54
See application file for complete search history.

(56) References Cited

U.S. PATENT DOCUMENTS

| | | | | |
|---|---|---|---|---|
| 2011/0312473 | A1* | 12/2011 | Chu | A63B 69/0053 482/54 |
| 2013/0035215 | A1* | 2/2013 | Ashby | A63B 22/0242 482/54 |
| 2013/0165297 | A1* | 6/2013 | Daly | A63B 24/00 482/9 |

OTHER PUBLICATIONS

"Ohki et al., Treadmill Motor Current Value Based Walk Phase Estimation, 2009, IEEE" (Year: 2009).*

* cited by examiner

*Primary Examiner* — Sundhara M Ganesan
*Assistant Examiner* — Shila Jalalzadeh Abyaneh
(74) *Attorney, Agent, or Firm* — WPAT, PC (57) ABSTRACT

The present invention discloses a running parameters detection system for treadmills and detection method thereof, wherein the system detects the running change data generated by a user running on a treadmill configured with a running belt, a motor and an electronic circuit device by means of a sensor, as well as the running belt operation speed data of the treadmill, in which the running change data is the current data or vertical acceleration data; subsequently, the running change data can be further applied to determine the touchdown moment recording point and the off-ground moment recording point, thereby then, based on such two time points, further calculating various kinematic parameters, e.g., touchdown time, in-the-air time, stride frequency, stride length and vertical amplitude or the like; for example, such five kinematic parameters can be utilized for scientifically monitoring and training runners.

7 Claims, 10 Drawing Sheets

RUNNING PARAMETERS DETECTION SYSTEM FOR TREADMILLS AND DETECTION METHOD THEREOF

BACKGROUND OF THE INVENTION

1. Field of the Invention

The present invention generally relates to a running parameters detection system for treadmills and detection method thereof; in particular, it relates to a running parameters detection system for treadmills and detection method thereof which are capable of using different sensors to detect data and further calculating such that it is possible to determine the characteristic values in each step when a person runs based on the variations in such detected data, thereby figuring out various kinematic parameters for scientifically monitoring and training running exercises.

2. Description of Related Art

In recent years, fitness and running sports are quite popular, and many organizations also organize various types of jogging activities such that people can participate and enjoy jogging outdoors. However, due to some factors, e.g., climate, weather etc., in case it is raining, cold, haze or the like in the open environment, it may be very unsuitable for outdoor running, so a lot of people may choose to use treadmills for indoor fitness purposes, and many large-scaled fitness locations may also install massive treadmills in the venue for customers to use.

Additionally, in the past, in order to obtain kinematics parameters during running, it is often necessary to rely on sophisticated and expensive instruments (e.g., high-speed cameras, force measurement boards, sole pressure insoles, etc.). However, these tools are not only inconvenient to apply, but the output data needs to be professionally processed so as to acquire the intended movement characteristics, and then can be further translated into kinematic parameters having actual application values by the interpretations of the professional sport science staff, and such entire processes may be very time-consuming and take significant amount of efforts. Moreover, due to the professional threshold thereof, it may be quite difficult to promote to public people, and often cannot provide real-time feedback in the moment of sports.

Therefore, compared to conventional methods, if the electric current information from the treadmill itself can be acquired and built-in analysis devices can operate conjunctively, it is possible to obtain kinematic parameters having application values and allow them to be real-time output during user's exercises, thus that the present invention provides an optimal solution.

SUMMARY OF THE INVENTION

The present invention discloses a running parameters detection system for treadmills and detection method thereof, comprising: a treadmill, including a running belt, a motor and an electronic circuit device electrically connected to the running belt and the motor, in which the electronic circuit device has: one or more sensors, which are used to detect the running change data generated by a user running on the running belt, wherein the running change data is the current data or the vertical acceleration data; a speed recorder, which is used for detecting and recording the running speed data from the running belt of the treadmill; a central processing electronic circuit assembly, which is connected to the sensors and the speed recorder and able to receive the running change data and the running belt operation speed data, wherein the central processing electronic circuit assembly internally includes: a touchdown recording unit, which is used to define the lowest point of each cycle in the running change data as the touchdown moment recording point; a stride frequency calculation unit, which is connected to the touchdown recording unit and able to determine the stride frequency data based on the number of the touchdown moment recording points recorded within a fixed duration of time; a stride length calculation unit, which is connected to the touchdown recording unit and is used to determine the stride length data based on the time between every two touchdown moment recording points and the running belt operation speed data; a transmission electronic circuit assembly, which is connected to the central processing electronic circuit assembly so as to transmit the data obtained from the calculations completed by the central processing electronic circuit assembly; and an electronic carrier, which can be connected to the electronic circuit device thereby receiving data calculated by the central processing electronic circuit assembly of the treadmill.

More specifically, the sensor can be a current sensor electrically connected to the motor thereby detecting the current data generated by the motor when the user is running on the running belt.

More specifically, the central processing electronic circuit assembly further includes an off-ground recording unit which is used to define the current chatter starting point before the touchdown moment recording point of each cycle in the current data as an off-ground moment recording point.

More specifically, the sensor can be an inertial sensor electrically connected to the treadmill thereby detecting the vertical acceleration data on the running belt when the user is running on the running belt.

More specifically, the central processing electronic circuit assembly further includes an off-ground recording unit which is used to define the maximum value before the touchdown moment recording point of each cycle in the vertical acceleration data as an off-ground moment recording point.

More specifically, the central processing electronic circuit component further includes a touchdown time calculation unit connected to the touchdown recording unit and the off-ground recording unit thereby determining the touchdown time data based on the time difference between each touchdown moment recording point to the next off-ground moment recording point.

More specifically, the central processing electronic circuit component further includes an in-the-air time calculation unit connected to the touchdown recording unit and the off-ground recording unit thereby determining the in-the-air time data based on the time difference between each off-ground moment recording point to the next touchdown moment recording point.

More specifically, the central processing electronic circuit component further includes a vertical amplitude calculation unit connected to the in-the-air time calculation unit thereby determining the vertical amplitude data by means of the in-the-air time data based on the Free Fall Formula.

More specifically, the electronic carrier is a handheld smart device, a tablet computer, a desktop computer, a panel or a notebook computer.

A running parameters detection method for treadmills, comprising:

(1) detecting the running change data generated by a user running on a treadmill including a running belt, a motor and an electronic circuit device through sensors as well as the operation speed data from the running belt of the treadmill, in which the running change data is the current data or the vertical acceleration data;

(2) determining the lowest point of each cycle in the running change data as a touchdown moment recording point;

(3) subsequently, determining the stride frequency data based on the number of the touchdown moment recording points within a fixed duration of time, and also further determining the stride length data based on the time between every two touchdown moment recording points and the running belt operation speed data; and (4) finally, transmitting the data calculated by the treadmill to an electronic carrier.

More specifically, the sensor can be a current sensor electrically connected to the motor thereby detecting the current data generated by the motor when the user is running on the running belt.

More specifically, it is possible to further define an off-ground moment recording point based on the current chatter starting point before the touchdown moment recording point of each cycle in the current data.

More specifically, the sensor can be an inertial sensor electrically connected to the treadmill thereby detecting the vertical acceleration data on the running belt when the user is running on the running belt.

More specifically, it is possible to further define an off-ground moment recording point based on the maximum value before the touchdown moment recording point of each cycle in the vertical acceleration data.

More specifically, it is possible to further define the touchdown time data based on the time difference from each touchdown moment recording point to the next off-ground moment recording point.

More specifically, it is possible to further define the in-the-air time data based on the time difference from each off-ground moment recording point to the next touchdown moment recording point.

More specifically, it is possible to further determine the vertical amplitude data by means of the in-the-air time data based on the Free Fall Formula.

More specifically, the electronic carrier is a handheld smart device, a tablet computer, a desktop computer, a panel or a notebook computer.

DETAILED DESCRIPTION OF THE PREFERRED EMBODIMENTS

Other technical contents, aspects and effects in relation to the present invention can be clearly appreciated through the detailed descriptions concerning the preferred embodiments of the present invention in conjunction with the appended drawings.

Figure 1A:
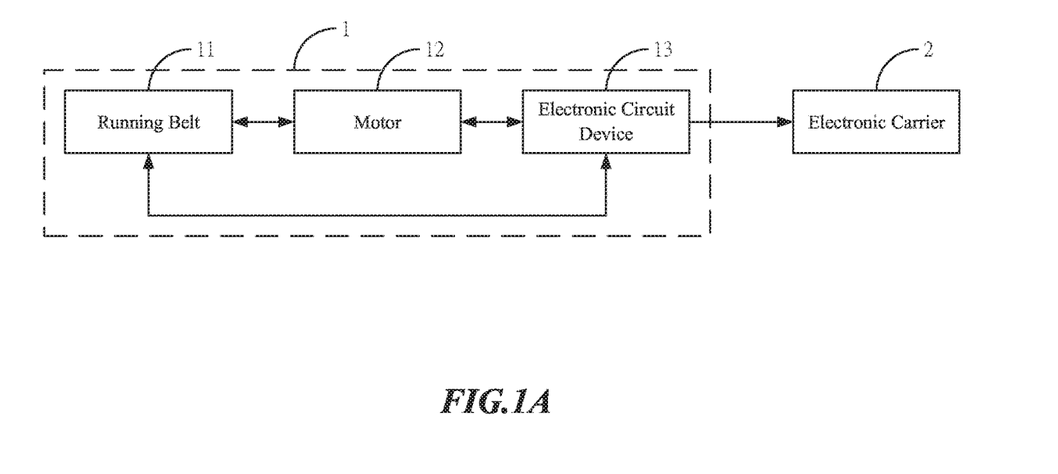
FIG. 1A shows an integral architecture view of the running parameters detection system for treadmills and detection method thereof according to the present invention.
Figure 1B:
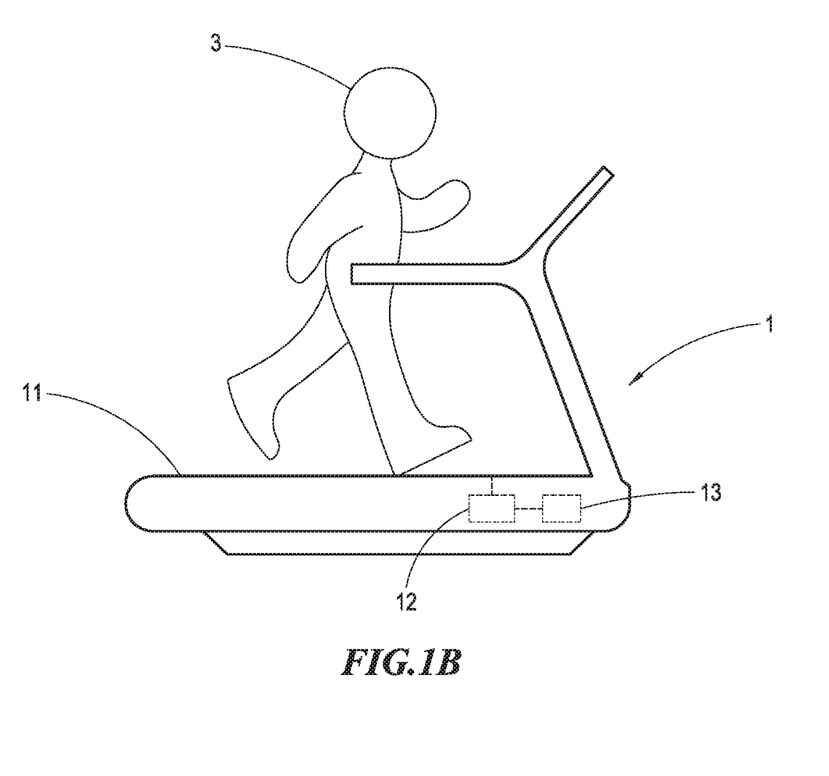
FIG. 1B shows a treadmill implementation view of the running parameters detection system for treadmills and detection method thereof according to the present invention.

Refer first to FIGS. 1A and 1B, wherein an integral architecture view and a treadmill implementation view of the running parameters detection system for treadmills and detection method thereof according to the present invention are respectively shown. It can be observed from such Figures that the present system comprises a treadmill 1 and an electronic carrier 2, wherein the treadmill 1 has a running belt 11, a motor 12, and a electronic circuit device 13 electrically connected to the running belt 11 and the motor 12, and the electronic circuit device 13 can receive data generated by a runner 3 running on the treadmill 1 and then transmit the received data to an electronic carrier 2, which may be, for example, a handheld smart device, a tablet computer, a desktop computer, a panel or a laptop computer or the like.

Figure 2A:
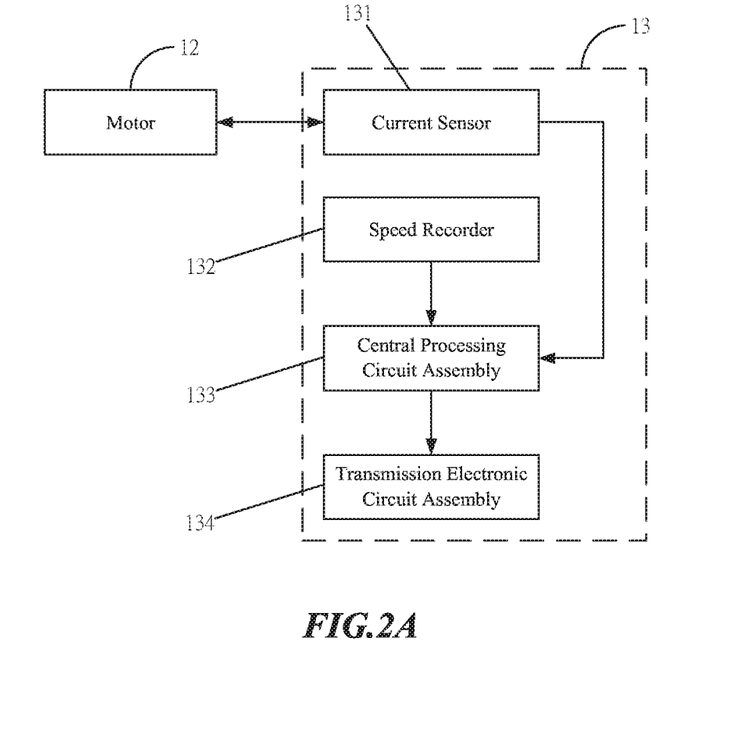
FIG. 2A shows a first implementation architecture view of the electronic circuit device in the running parameters detection system for treadmills and detection method thereof according to the present invention.

As shown in FIG. 2A, it can be seen that the electronic circuit device 13 is composed of one or more circuit boards, and the circuit board of the circuit device 13 includes one or more sensors (e.g., current sensor 131), a speed recorder 132, a central processing electronic circuit assembly 133 and a transmission electronic circuit assembly 134, wherein the current sensor 131 is used to detect the running change data (current data) generated by the motor 12 when the user runs on the running belt 11, the speed recorder 132 is used to detect and record the running belt operation speed data from the running belt of the treadmill 1, and the transmission electronic circuit assembly 134 is used to transmit the data after the calculation of the central processing electronic circuit assembly 133 (or alternatively, not designed within the electronic circuit device 13, but such sensors and speed recorder may be otherwise directly configured inside the treadmill 1, and then the detected data may be sent to the electronic circuit device 13 for calculations).

Figure 2B:
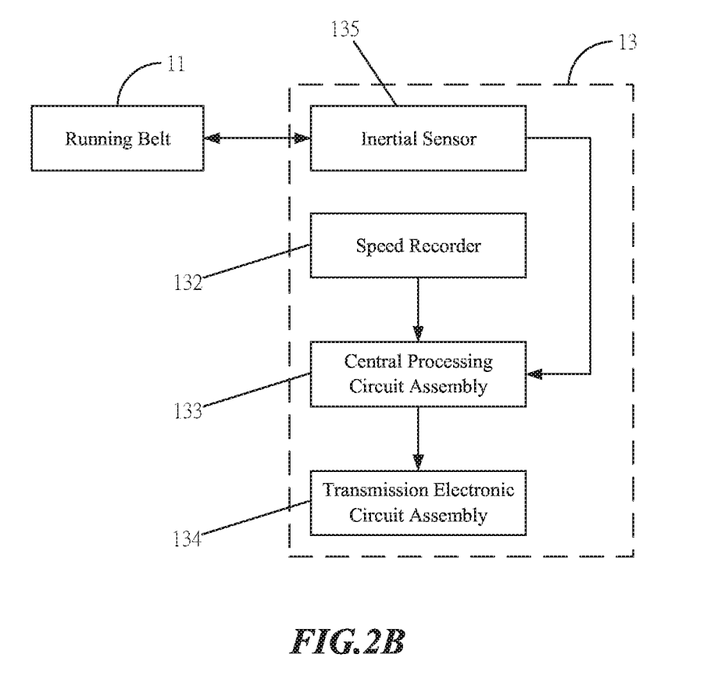
FIG. 2B shows a second implementation architecture view of the electronic circuit device in the running parameters detection system for treadmills and detection method thereof according to the present invention.

In addition to the current sensor 131, it is also possible, as shown in FIG. 2B, the sensor may be an inertial sensor 135 electrically connected to the treadmill 1 thereby detecting the vertical acceleration data on the running belt 11 when the user is running thereon.

Figure 4A:
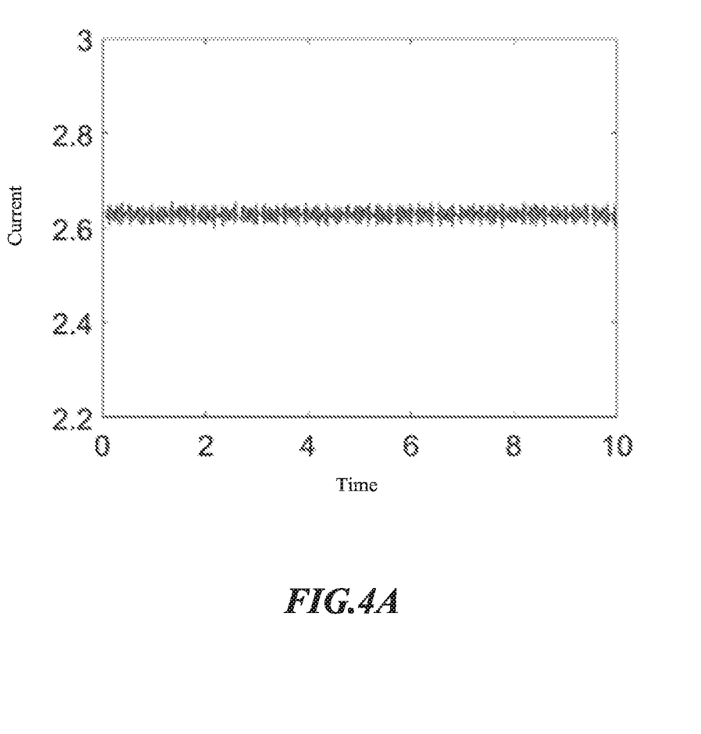
FIG. 4A shows a current signal view of the first implementation architecture view of the electronic circuit device in the running parameters detection system for treadmills and detection method thereof according to the present invention, which is under an Idling state.
Figure 4B:
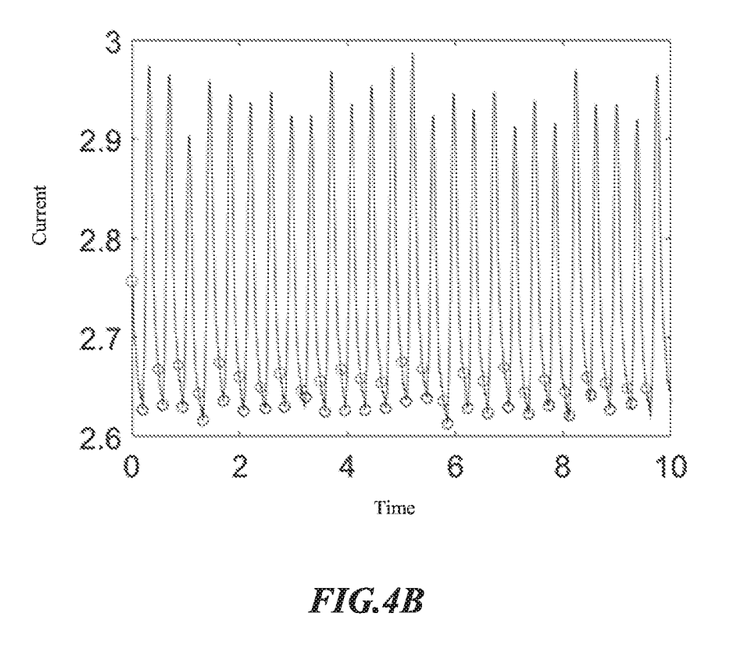
FIG. 4B shows a current signal view of the first implementation architecture view of the electronic circuit device in the running parameters detection system for treadmills and detection method thereof according to the present invention, which is under a running state.
Figure 5A:
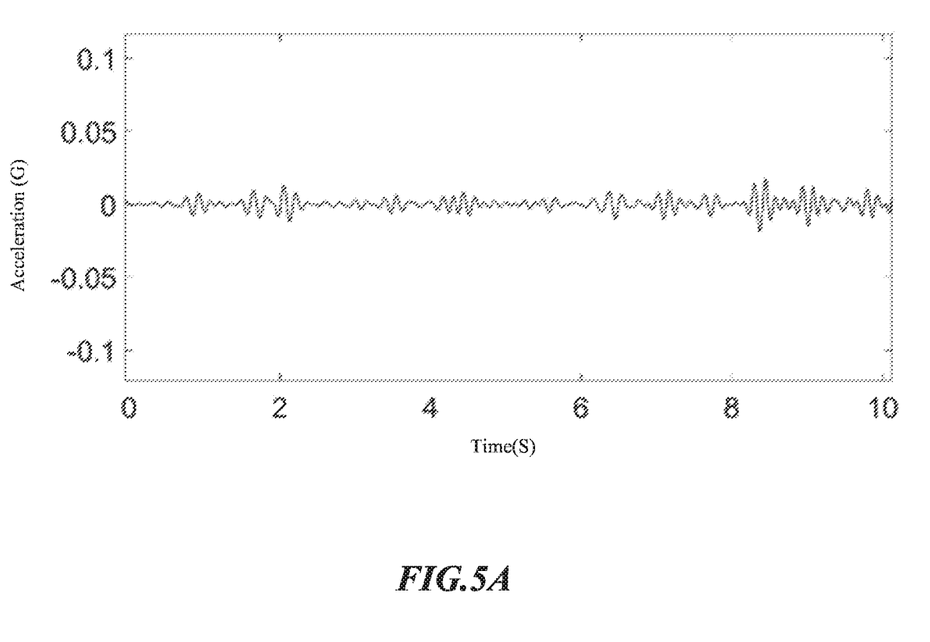
FIG. 5A shows an acceleration signal view of the second implementation architecture view of the electronic circuit device in the running parameters detection system for treadmills and detection method thereof according to the present invention, which is under an Idling state and along the IMU vertical direction.
Figure 5B:
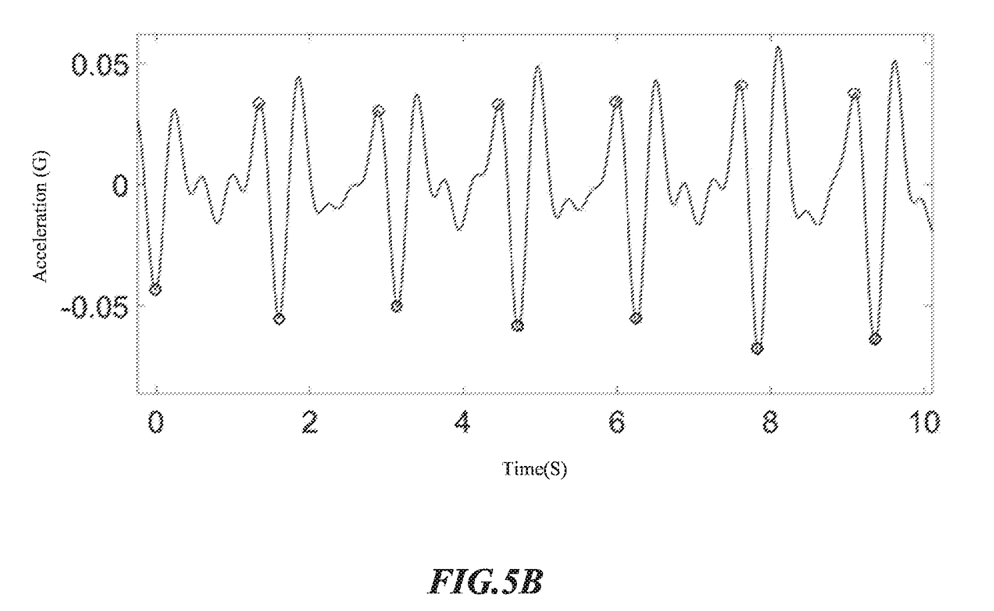
FIG. 5B shows an acceleration signal view of the second implementation architecture view of the electronic circuit device in the running parameters detection system for treadmills and detection method thereof according to the present invention, which is under a running state and along the IMU vertical direction.

To illustrate with an actual treadmill, seeing that changes in the motor current sensor and the inertial sensor (IMU) may correspondingly vary because of external loads, when the treadmill is idle for 10 seconds, as shown in FIG. 4A, the current demonstrates a stable output, and the IMU (vertical acceleration) signals also fluctuate only slightly, as shown in FIG. 4B. But when a person is running, the conditions in the current sensor 131 and the inertial sensor 135 can be respectively described, as follows:

(1) Current Sensor:

The runner 3 is stepping on the running belt 11 of the treadmill 1 which may inhibit the running belt 11 from rotating, so the current of the treadmill 1 is adjusted and changed, as shown in FIG. 4B. Therefore, from the current diagram, it is obvious that when the foot touches the ground, the current will rise sharply, so the wave valley shown on the Figure can represent the moment that each time the foot touches the ground (marked by the lower circle on FIG. 4B), and then, after the foot leaving the ground, there will be a period of vibration or chattering in the current due to the instability of the force, which can be used to calculate the time point when the foot is off the ground (marked by the upper circle on the Figure);

(2) Inertial Sensor:

Because the treading of runner 3 will cause the acceleration of the treadmill 1 to change in the vertical direction (as shown in FIG. 5B), from the IMU diagram, it can be seen that when the foot touches the ground, the acceleration in the vertical direction will increase sharply; hence, the lowest point of each cycle can represent the moment when the foot touches the ground (marked by the lower circle on FIG. 5B), and then, after the foot leaving the ground, the treadmill 1 will generate upward acceleration due to the ground reaction force, the maximum before the wave valley can represent the moment when the toes are off the ground (marked by the upper circle on FIG. 5B).

Figure 3:
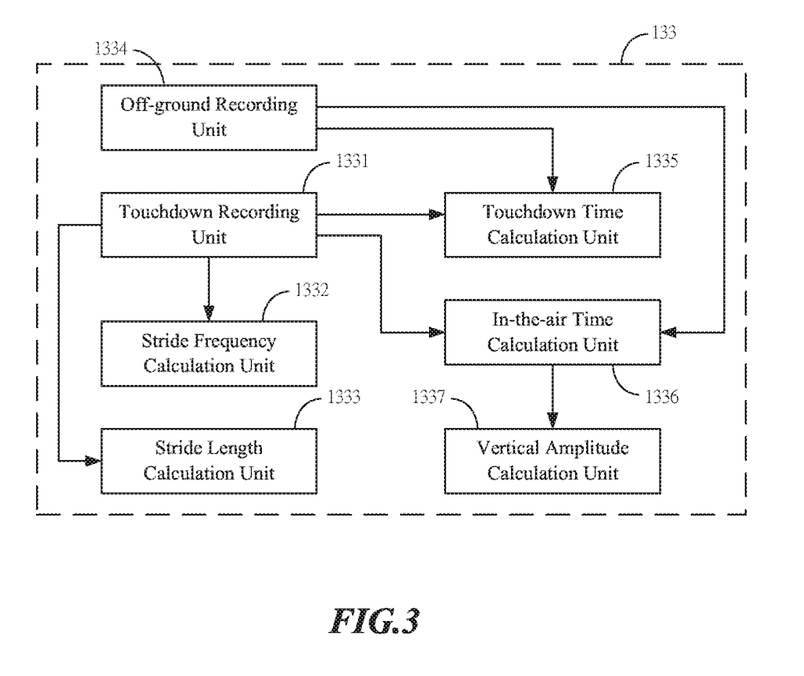
FIG. 3 shows an architecture view of the central processing electronic circuit assembly in the running parameters detection system for treadmills and detection method thereof according to the present invention.

Moreover, as shown in FIG. 3, the central processing electronic circuit assembly 133 can receive the running change data and the running belt operation speed data, wherein the central processing electronic circuit assembly includes a touchdown recording unit 1331, a stride frequency calculation unit 1332, a stride length calculation unit 1333, an off-ground recording unit 1334, a touchdown time calculation unit 1335, an in-the-air time calculation unit 1336 and a vertical amplitude calculation unit 1337; herein the touchdown recording unit 1331 is applied to define the lowest point of each cycle in the data as the touchdown moment recording point.

Since the stride frequency indicates the number of foot touchdowns on the ground within one minute, the higher the frequency is, the lower the probability of running injury becomes; therefore, the stride frequency calculation unit 1332 can determine the stride frequency data based on the number of the touchdown moment recording points within a fixed duration of time (for example, when it receives the data that the number of touchdowns within 10 seconds is 12 times, then the stride frequency can be calculated as 12*(60/10)=72 times/minute).

Besides, the stride length is calculated according to the formula (Distance=Speed*Time), and the (time between two touchdowns)*(the current speed of the treadmill) allows to derive the stride length, so the stride length calculation unit 1333 is used to determine the stride length data based on the time between every two touchdown moment recording points and the running belt operation speed data (for example, when the running speed is 7 km/hr, and the time between two off-ground separations=0.34−0.12=0.22 seconds, so the stride length can be calculated to be 0.22*(700000/3600)=42.77 cm).

In case the sensor is a current sensor 131, the off-ground recording unit 1334 can define an off-ground moment recording point based on the current chatter starting point before the touchdown moment recording point of each cycle in the current data. Suppose the sensor is an inertial sensor 135, the off-ground recording unit 1334 can define an off-ground moment recording point based on the maximum value before the touchdown moment recording point of each cycle in the vertical acceleration data.

Since the touchdown time refers to the duration of time after the foot touches the ground until it is off the ground, for runners, a shorter touchdown time is a more efficient approach, and the touchdown time calculation unit 1335 is used to determine the touchdown time data based on the time difference from each touchdown moment recording point to the next off-ground moment recording point (for example, suppose the touchdown moment recording point is 6.6 second, the off-ground moment recording point is 6.94 second, then the touchdown time data is 6.94−6.6=0.34 second).

In addition, opposite to the touchdown time, the in-the-air time refers to a duration of time when the foot leaves the ground until it touch the ground again, so it can be understood that the longer the in-the-air time is, the less effort it takes to run. Therefore, the in-the-air time calculation unit 1336 can determine the in-the-air time data based on the time difference from each off-ground moment recording point to the next touchdown moment recording point (for example, if the off-ground moment recording point is 6.94 second, and the next touchdown moment recording point is 7.06 second, then the in-the-air time is 7.06−6.94=0.12 second).

Moreover, the vertical amplitude indicates the up-down vibration amplitude of the body's center of mass during running, so the present system can calculate the vertical amplitude during running according to the Free-Fall formula; consequently, the vertical amplitude calculation unit 1337 can further determine a vertical amplitude data according to the Free-Fall formula (for example, if the in-the-air time is 0.12 second, then the vertical amplitude is 0.5*9.8*((0.12/2)^2)=0.0176=1.7 cm).

Figure 6:
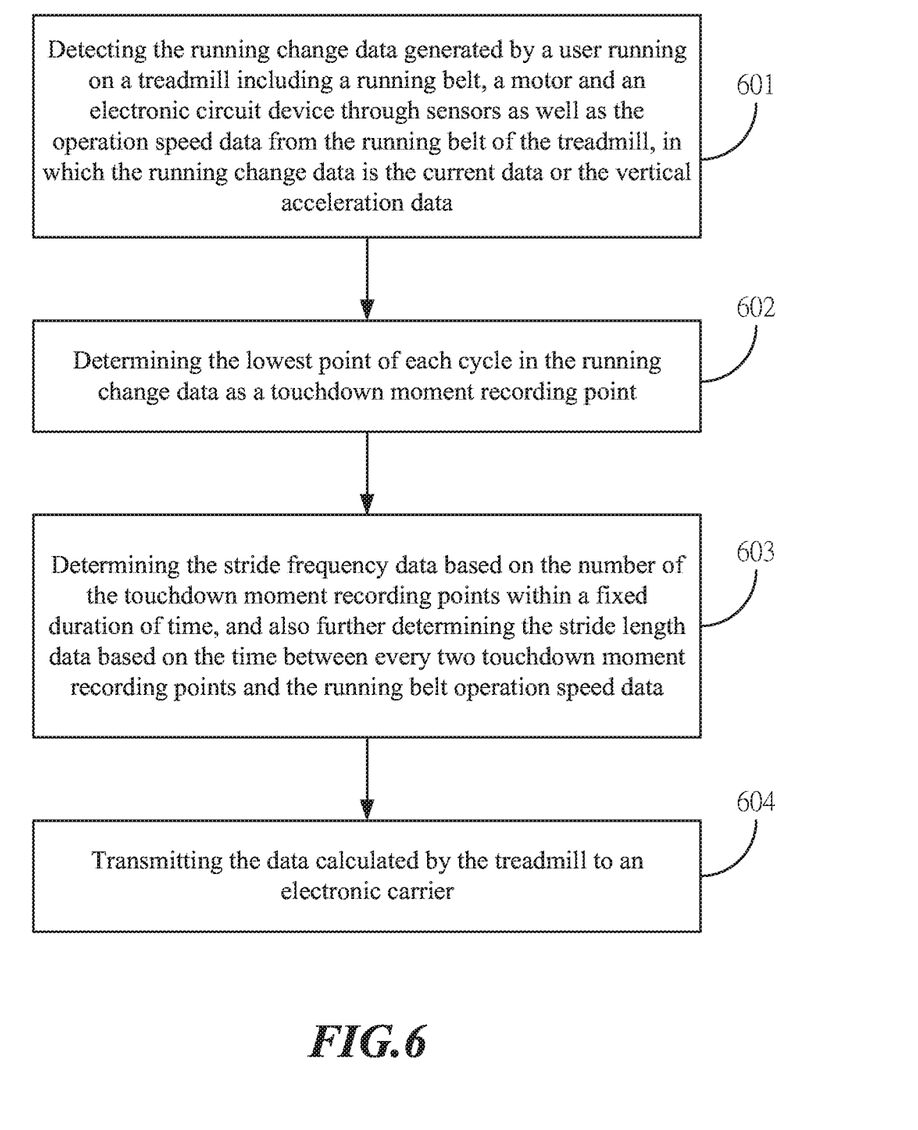
FIG. 6 shows a flowchart of the detection method in the running parameters detection system for treadmills and detection method thereof according to the present invention.

Furthermore, the detection method flowchart is shown in FIG. 6, and steps thereof are described in details as below:

(1) detecting the running change data generated by a user running on a treadmill including a running belt, a motor and an electronic circuit device through sensors as well as the operation speed data from the running belt of the treadmill, in which the running change data is the current data or the vertical acceleration data (601);

(2) determining the lowest point of each cycle in the running change data as a touchdown moment recording point (602);

(3) subsequently, determining the stride frequency data based on the number of the touchdown moment recording points within a fixed duration of time, and also further determining the stride length data based on the time between every two touchdown moment recording points and the running belt operation speed data (603); and (4) finally, transmitting the data calculated by the treadmill to an electronic carrier (604).

Compared with other prior arts, the running parameters detection system for treadmills and detection method thereof according to the present invention provides the following advantages:

(1) The present invention can capture the current or vertical acceleration information of the treadmill itself and operate in conjunction with the built-in analysis devices to output in real-time kinematic parameters having application values during a user's sport time.

(2) Upon obtaining the desired kinematics parameters, the present invention needs not to neither rely on external or additional instruments nor professional sport-science staffs for post analyses, but simply to first obtain the electrical current or vertical acceleration information of the treadmill itself, then, based on these two types of data, it is possible to determine various kinematic parameters (e.g., touchdown time, in-the-air time, stride frequency, stride length, and vertical amplitude, etc.) which are commonly used in scientific running supervising and training processes.

It should be noticed that, although the present invention has been disclosed through the detailed descriptions of the aforementioned embodiments, such illustrations are by no means used to restrict the scope of the present invention; that is, skilled ones in relevant fields of the present invention can certainly devise any applicable alterations and modifications after having comprehended the aforementioned technical characteristics and embodiments of the present invention without departing from the spirit and scope thereof. Hence, the scope of the present invention to be protected under patent laws should be delineated in accordance with the claims set forth hereunder in the present specification.

What is claimed is:

1. A running parameters detection system for treadmills, comprising:
    a treadmill, including a running belt, a motor and an electronic circuit device electrically connected to the running belt and the motor, the electronic circuit device having:
    one or more sensors, used to detect running change data generated by a user running on the running belt, wherein the one or more sensors includes a current sensor electrically connected to the motor thereby detecting motor current data generated by the motor when the user is running on the running belt, the running change data including the motor current data;
    a speed recorder, used for detecting and recording a running belt operation speed data from the running belt of the treadmill;
    a central processing electronic circuit assembly, connected to the one or more sensors and the speed recorder and able to receive the running change data and the running belt operation speed data, wherein the central processing electronic circuit assembly internally includes:
    a touchdown recording unit, used to define the lowest point of each cycle in the running change data as a corresponding touchdown moment recording point;
    a stride frequency calculation unit, connected to the touchdown recording unit and able to determine stride frequency data based on a number of the corresponding touchdown moment recording points recorded within a fixed duration of time;
    a stride length calculation unit, connected to the touchdown recording unit and is used to determine stride length data based on the time between each consecutive two touchdown moment recording points and the running belt operation speed data; and
    an off-ground recording unit, used to identify at least a current chatter starting point before each touchdown moment recording point of each cycle in the motor current data to calculate a time point as an off-ground moment recording point;
    a transmission electronic circuit assembly, connected to the central processing electronic circuit assembly so as to transmit the data obtained from the calculations completed by the central processing electronic circuit assembly; and
    an electronic carrier, connected to the electronic circuit device thereby receiving data calculated by the central processing electronic circuit assembly of the treadmill.

2. The running parameters detection system for treadmills according to claim 1, wherein the central processing electronic circuit assembly further includes an in-the-air time calculation unit connected to the touchdown recording unit and the off-ground recording unit thereby determining in-the-air time data based on a time difference between each off-ground moment recording point to the next respective touchdown moment recording point.

3. The running parameters detection system for treadmills according to claim 2, wherein the central processing electronic circuit assembly further includes a vertical amplitude calculation unit connected to the in-the-air time calculation unit thereby determining vertical amplitude data based on the in-the-air time data using Free Fall Formula.

4. The running parameters detection system for treadmills according to claim 1, wherein the central processing electronic circuit assembly further includes a touchdown time calculation unit connected to the touchdown recording unit and the off-ground recording unit thereby determining touchdown time data based on a time difference between each touchdown moment recording point and a respective next off-ground moment recording point.

5. The running parameters detection system for treadmills according to claim 1, wherein the central processing electronic circuit assembly further includes a touchdown time calculation unit connected to the touchdown recording unit and the off-ground recording unit thereby determining touchdown time data based on a time difference between each touchdown moment recording point and a respective next off-ground moment recording point, the central processing electronic circuit assembly further includes an in-the-air time calculation unit connected to the touchdown recording unit and the off-ground recording unit thereby determining in-the-air time data based on a time difference between each off-ground moment recording point to the next respective touchdown moment recording point, and the central processing electronic circuit assembly further includes a vertical amplitude calculation unit connected to the in-the-air time calculation unit thereby determining vertical amplitude data based on the in-the-air time data using Free Fall Formula.

6. A running parameters detection method for treadmills, comprising:
    detecting running change data generated by a user running on a treadmill including a running belt, a motor and an electronic circuit device having one or more sensors and a speed recorder, wherein the detecting running change data comprises detecting, by the one or more sensors, motor current data generated by the motor when the user is running on the running belt, the running change data including the motor current data;

detecting, by the speed recorder, running belt operation speed data from the running belt of the treadmill;

determining the lowest point of each cycle in the running change data as a corresponding touchdown moment recording point;

determining stride frequency data based on a number of the corresponding touchdown moment recording points within a fixed duration of time, and also further determining the stride length data based on the time between each consecutive two touchdown moment recording points and the running belt operation speed data;

identifying at least a current chatter starting point before each touchdown moment recording point of each cycle in the motor current data to calculate a time point as an off-ground moment recording point; and transmitting the data calculated by the treadmill to an electronic carrier.

7. The running parameters detection method for treadmills according to claim 6, wherein the one or more sensors comprising a current sensor electrically connected to the motor thereby detecting the motor current data generated by the motor when the user is running on the running belt.

* * * * *